United States Patent [19]

LaRose

[11] Patent Number: 5,237,112
[45] Date of Patent: Aug. 17, 1993

[54] PROCESS FOR TETRABROMOBISPHENOL-A

[75] Inventor: David E. LaRose, Baton Rouge, La.

[73] Assignee: Ethyl Corporation, Richmond, Va.

[21] Appl. No.: 934,383

[22] Filed: Aug. 31, 1992

[51] Int. Cl.$^5$ .......................................... C07C 39/367
[52] U.S. Cl. .................................. 568/726; 568/722; 568/723; 568/728
[58] Field of Search ............... 568/722, 726, 779, 728, 568/723

[56] References Cited

U.S. PATENT DOCUMENTS

| | | | |
|---|---|---|---|
| 3,929,907 | 12/1975 | Janzon et al. | 260/619 R |
| 4,075,119 | 2/1978 | Schmidt et al. | 252/182 |
| 4,180,684 | 12/1979 | Kleinschmit et al. | 568/726 |
| 4,210,765 | 7/1980 | Mark | 568/726 |
| 4,283,566 | 8/1981 | Mark | 568/726 |
| 5,068,463 | 11/1991 | Walter | 568/726 |
| 5,107,035 | 4/1992 | Hines et al. | 568/726 |
| 5,138,103 | 8/1992 | Eguchi et al. | 568/726 |

FOREIGN PATENT DOCUMENTS

| | | |
|---|---|---|
| 7420082 | 1/1976 | France. |
| 64410 | 3/1985 | Israel. |
| 58728 | 5/1979 | Japan. |
| 225034 | 12/1983 | Japan. |
| 049742 | 3/1987 | Japan. |
| 316748 | 12/1988 | Japan. |

OTHER PUBLICATIONS

"Copolycarbonates of bisphenol-A and tetrahalobisphenol-A; Synthesis of tetrahalobisphenols-A: Part I," Pop. Plast. Rubber 26(1), 3-9, (1981).
"Tetrahalogenated 4:4'-Dihydroxydiphenylalkanes, their Synthesis and some of their Reactions," Egypt. J. Chem. 20 No. 5, pp. 483-490 (1977).
"Oxidative Bromination of 2,2-Bis (4'Hydroxyphenyl)-Propane," Institute of Organochlorine Synthesis, Academy of Sciences of the Azerbaidzhan SSR, Sumgait, (1989).
Chemical Abstracts 101 (26):231164p.
Chemical Abstracts 102 (8):62672d.
Chemical Abstracts 102 (10):79427a.
Chemical Abstracts 105 (18):155068p.
Chemical Abstracts 109 (13):110003e.
Chemical Abstracts 110 (20):173951d.

Primary Examiner—Werren B. Lone
Attorney, Agent, or Firm—David E. LaRose

[57] ABSTRACT

This invention relates to a process for preparing tetrabromobisphenol-A in high yield and high purity comprising: (a) forming a reaction solvent from at least one non-polar solvent and an amount of aqueous hydrogen peroxide; (b) charging an amount of alkylidenediphenol to the reaction solvent to form a reaction mass; (c) feeding an amount of bromine to the reaction mass at a temperature and for a period of time sufficient to tetrabrominate substantially all of the alkylidenediphenol thus charged; (d) maintaining during step (c) the amount of hydrogen peroxide less than an amount required to convert substantially all of the HBr which forms to elemental bromine; and (e) heat treating the formed product whereby a product having less than about 20 ppm ionic impurities is produced.

22 Claims, No Drawings

PROCESS FOR TETRABROMOBISPHENOL-A

BACKGROUND

This invention relates to a process for the production of tetrabromo-4,4'-alkylidenediphenols, commonly referred to as tetrabromobisphenol-A (TBBPA). The process of this invention is based on the bromination of alkylidenediphenols in the presence of an organic solvent and the subsequent treatment of the recovered product whereby a high yield of high quality TBBPA product is obtained.

Nuclear brominated phenolic compounds, such as tetrabromobisphenol-A (TBBPA) and tribromophenol, are used in plastic materials and synthetic resins as flameproofing agents. TBBPA is particularly important for this purpose, since it can be incorporated reactively into polymers systems, for instance epoxy resins and polyesters, via the two phenolic hydroxyl groups. For this application, it is desirable to use high quality TBBPA. The products must be as free as possible from byproducts, have good color characteristics and be essentially free from impurities. Due to the need for such high quality TBBPA products, there continues to be a need for improved processes for the formation of such highly purified products.

THE INVENTION

There has now been developed a process for preparing brominated alkylidenediphenol, especially, 4,4'-isopropylidenebis (2,6-dibromophenol) hereinafter referred to as TBBPA, in high yield and containing less than about 20 ppm ionic impurity. The process comprises: a) forming a reaction solvent from at least one non-polar solvent and an amount of aqueous hydrogen peroxide; (b) charging an amount of alkylidenediphenol to the reaction solvent to form a reaction mass; (c) feeding an amount of bromine to the reaction mass at a temperature and for a period of time sufficient to tetrabrominate substantially all of the alkylidenediphenol thus charged; (d) maintaining during step (c) the amount of hydrogen peroxide less than an amount required to convert substantially all of the HBr which forms, to elemental bromine; and (e) heat treating the formed product whereby a product having less than about 20 ppm ionic impurities is produced. The yield of pure substance obtained in the process of this invention is at least as high as the yield obtained in known processes. For the purposes of this invention, the term "ionic impurity" is used to refer to inorganic bromides—particularly HBr.

The reaction solvent is a mixture of non-polar solvent and a co-solvent optionally containing an amount of aqueous hydrogen peroxide which is less than the amount of hydrogen peroxide required to convert substantially all of the HBr which forms, to elemental bromine. The reaction solvent thus provides a reaction medium which results in a reduction in product contamination and unwanted side reactions. Non-polar solvents which are inert towards the reactants, but which allow the tetrabromo compounds to be crystallized out are most preferred. The non-polar solvent is selected such that there is also limited miscibility of the non-polar solvent with water. Suitable non-polar solvents include tetrachloroethylene, chlorobenzene, carbon tetrachloride, ethylene dibromide, ethylene dichloride, chloroform, fluorobenzene, 1,1,2-tri-chloroethane, 1,1,1-trichloroethane, propylene dichloride, dibromotetrafluoroethane, trichlorotrifluoroethane, butyl chloride, amyl chloride, hexyl chloride, benzene, toluene, o-xylene, m-xylene, p-xylene, pentane, n-hexane, n-octane, n-decane, gasoline, petroleum ether, and mixtures of any two or more of the foregoing. Organic non-polar solvents with a boiling point in the range of from about 80° to about 200° C., especially about 80° to about 150° C. are preferred, such as chlorobenzene, tetrachloroethylene, and fluorobenzene, with chlorobenzene being the most preferred.

If it is desirable to form both TBBPA and HBr co-products, then the amount of aqueous hydrogen peroxide used in the process of this invention is optional. When used, the aqueous hydrogen peroxide co-solvent preferably contains from about 30 to about 70 weight percent hydrogen peroxide in water, more preferably from about 40 to about 60 weight percent hydrogen peroxide, and most preferably about 50 weight percent hydrogen peroxide. It is most desirable to use aqueous hydrogen peroxide which has been acidified by dilute mineral acid. Such mineral acids include, sulfuric acid, phosphoric acid, nitric acid and the like. Preferably, the mineral acid is sulfuric acid and the sulfuric acid is added to the aqueous hydrogen peroxide in an amount ranging from about 1 to about 5 weight percent, most preferably about 3 weight percent of the aqueous hydrogen peroxide solution.

The amount of aqueous hydrogen peroxide used typically ranges from about 0.05 to less than about 1.0 moles of hydrogen peroxide per mole of bromine charged to the reaction vessel. Since for each mole of bromine reacted, there is formed one mole of HBr, not all of the HBr thus formed will be oxidized to $Br_2$ in the absence of a stoichiometric amount of hydrogen peroxide. Thus, the reaction mass will contain HBr as a co-product. If no co-product HBr is desired to be formed, then the amount of hydrogen peroxide should be in excess of the stoichiometric amount required to oxidize essentially all of the HBr thus formed to $Br_2$. A molar excess of about 1 to about 5 percent hydrogen peroxide per mole of HBr is generally sufficient to convert essentially all of the HBr to $Br_2$. Alternatively, the reaction can be performed in the substantial absence of aqueous hydrogen peroxide when it is desirable to form a significant amount of HBr byproduct. In the absence of hydrogen peroxide there will be formed about four moles of HBr per mole of TBBPA. Thus the process of this invention provides significant flexibility for varying the amount of HBr co-product formed.

When used, the amount of aqueous hydrogen peroxide to non-polar solvent will depend essentially on the type of non-polar solvent selected. Generally, it is advantageous to so choose the non-polar solvent such that for one part by volume of aqueous phase, there will be about 1 to about 20 parts non-polar solvent phase. Particularly preferred is about 1 to about 10 parts non-polar solvent per part of aqueous phase. In the absence of aqueous hydrogen peroxide, the same proportion of non-polar solvent to water is desirably used.

Alkylidenediphenol is charged to the reaction solvent in order to form a reaction mass. Typically the weight percent of alkylidenediphenol to reaction solvent should be greater than about 10 weight percent, more preferably from about 21 to about 32 weight percent and most preferably from about 22 to about 29 weight percent alkylidenediphenol to solvent.

Subsequent to forming the reaction mass, an amount of bromine is fed to the reaction mass which is sufficient to provide at least four gram atoms of bromine per mole of alkylidenediphenol. Generally, it is advantageous to use an excess of bromine due to side reactions resulting from the bromination of impurities present in the alkylidenediphenol reactant and due to the formation of HBr. Preferably, bromine is provided in an excess of from about 1 to about 5 mole percent preferably from about 2 to about 3 mole percent excess based on the amount of bromine required to tetra-brominate the alkylidenediphenol. When hydrogen peroxide is used, and the formation of HBr is minimized, the amount of bromine fed to the reaction vessel is preferably in the range of from about 2.05 to about 2.5 mole of bromine per mole of alkylidenediphenol charged to the reaction vessel. Up to about 4.0 moles of bromine may be fed to the reaction vessel when the formation of HBr is not minimized by the addition of a sufficient amount of hydrogen peroxide to oxidize all of the HBr thus formed. In the absence of using hydrogen peroxide to oxidize HBr, the amount of bromine fed to the reaction vessel is preferably from about 4.0 to about 4.5 moles of bromine per mole of alkylidenediphenol charged to the reaction vessel.

For the purposes of this invention, the order of addition of reactants is not critical. However, it is highly preferred to charge the bromine to the reaction mass containing the non-polar solvent, aqueous hydrogen peroxide or water, and alkylidenediphenol.

The bromination reaction is conducted at a temperature below about 60° C., preferably below about 50° C., more preferably from about 0° to about 35° C., and most preferably from about 0° to about 25° C. Since the reaction is exothermic, refrigeration may be required to maintain the reaction mass at the desired temperature. Although the pressure can be selected at random within a wide range, it is advantageous in order to use less expensive equipment to operate at atmospheric pressure or slightly above atmospheric pressure Depending on the reaction temperature, superatmospheric pressure may be used in order to maintain the HBr which forms in the reaction vessel.

Once the bromine addition is complete, the TBBPA is maintained in suspension in the reaction solvent by rapid agitation. The reaction mass is then heated to a temperature sufficient to dissolve essentially all of the TBBPA in the non-polar solvent phase. Again, the temperature depends on the particular non-polar solvent chosen. For the preferred chlorobenzene solvent, the temperature is about 80° C. Once dissolved, the aqueous phase containing mineral acid, unreacted hydrogen peroxide (when used), and HBr can be separated from the organic phase containing the product. The HBr co-product separated from the reaction mass in the aqueous phase can be further purified or concentrated by well known techniques such as absorption, distillation, extraction, and the like.

The non-polar solvent phase containing the TBBPA product is then contacted with an aqueous alkali sulfite solution such as $Na_2SO_3$ and rinsed with deionized water. The amount of $Na_2SO_3$ in the aqueous solution is in the range of from about 25 to about 100 grams of $Na_2SO_3$ per kilogram of TBBPA product. Preferably, the aqueous solution contains 10 to 15% $Na_2SO_3$ by weight. Several sulfite contacts and water rinses may be used depending on the impurities in the TBBPA product. Contact time of the non-polar solvent phase containing the product with the sulfite solution may range from 1 minute to 2 hours or more. However, a contact time of 5 to 20 minutes is generally sufficient. After each contact and water rinse, the aqueous phase is separated from the non-polar solvent phase. It is important to maintain the temperature during the sulfite contact and water rinse such that the TBBPA product remains in solution in the non-polar solvent phase.

After contacting the non-polar solvent phase containing the TBBPA product with sulfite, the non-polar solvent phase is allowed to cool to a temperature wherein the TBBPA product crystallizes out, generally about 20° C. The crystallization and separation of the crystals from the mother liquor are carried out according to the generally known methods and by using conventional solid-liquid separation devices such as filters and/or centrifuges. Additional deionized water wash of the crystallized product may then take place during the separation of the product crystals from the mother liquor. The product filter cake may also be rinsed with deionized water before removal of the product filter cake from the filter or centrifuge.

A key feature of this invention is the step of heat treating the TBBPA predominant product at a temperature and for a period of time which are sufficient to reduce the amount of total ionic impurity in the thus treated product. When heat treating the product, the temperature is generally above about 110° C. Preferably, the temperature is in a range of from about 120° C. to about 180° C., and most preferably in a range of from about 130° C. to about 175° C. Higher or lower temperatures may also be used. However, the temperature should not be so high as to cause melting or degradation of the TBBPA predominant product. Typically, TBBPA melts at a temperature of about 180° C. Thus the practical upper limit of the heat treating temperature is about 175° C. At a temperature lower than the preferred temperature, a longer heating time may be required to achieve the desired results.

The heat treating time required to obtain the enhanced quality product is related to the temperature used for the heat treating. At a temperature above about 120° C., the time for heat treating the product is preferably greater than about 10 seconds. A preferred residence time for heat treating a product predominant in TBBPA ranges from about 30 seconds to about 1 hours with the most preferred time ranging from about 5 minutes to about 30 minutes.

The time required may also depend on the equipment selected for the heat treating process. Equipment which may be useful in the process of this invention include the Wyssmont TURBO-DRYER and the Bepex TORUSDISC Dryer, e.g. TORUSDISC Model TDJ2611 and the like. Those skilled in the art can readily select heat treating equipment based on the above residence times and temperatures in order to obtain the desired low impurity product.

It has been found, quite unexpectedly, that rinsing the product with deionized water prior to the heat treating step has a significant beneficial effect on the quality of product thus produced. For the purposes of this invention, the deionized water preferably has a resistivity of greater than about 50,000 ohms, more preferably, greater than about 100,000 ohms, and most preferably greater than about 500,000 ohms. Such deionized water can be prepared by contacting the water with commercially available ion exchange resin until the resistivity of the water is greater than about 50,000 ohms. Higher resistivities can be obtained by treating the water in any one or more commercially available reverse osmosis units and subsequently contacting the water with an ion exchange resin. In the latter case, resistivities of greater than 500,000 ohms, typically greater than 1,000,000 ohms may be obtained. While it is desirable to contact the TBBPA predominant product with deionized water having a resistivity as high as economically possible, good results may be obtained by contacting the TBBPA product with deionized water having a resistivity at least about 50,000 ohms. The methods of preparing deionized water having the foregoing resistivities is well known by those skilled in the art.

The amount of deionized water used in contacting the TBBPA predominant product is that amount sufficient to enhance the quality of the product to the desired degree. Preferably, the product is contacted with at least about 0.1 grams of deionized water per gram of product. More preferably, the product is contacted with at least about 0.2 grams of deionized water per gram of product, and most preferably with about 0.3 to about 0.5 grams of deionized water per gram of product. There is no real upper limit on the amount of deionized water to use in contacting the product, however, economic considerations and manufacturing equipment limitations provide that only the amount of water required to enhance the quality of product to the desired degree need be used.

While it may be beneficial to contact the product with deionized water at any stage of the process for preparing TBBPA, in general, the contacting need only be done after or during the procedure for separating the TBBPA predominant product from the reaction mass slurry. The separation of the TBBPA predominant product from the reaction mass slurry may be accomplished by filtering or centrifuging the product solids. In the filtering or centrifuging operation, a major amount of aqueous HBr is removed from the solid product in the centrate or filtrate. However, residual HBr impurity remains in the solid product obtained from the centrifuge. The residual HBr impurity contributes to the total ionic impurity in the solid product.

The process of this invention may be illustrated by the following non-limiting examples.

EXAMPLE 1

Preparation of 4,4'-isopropylidene-bis(2,6-dibromophenol)

Chlorobenzene (800 mL) together with 2.1 moles per mole of bisphenol-A of a 50% by weight aqueous solution of hydrogen peroxide (acidified with 3% by weight $H_2SO_4$) and bisphenol-A are charged to an enamelled stirred vessel. The reaction mass is vigorously stirred and bromine (2.06 moles per mole of bisphenol-A) is metered into the agitated solution. The heat of reaction is removed by circulating a portion of the reaction mass through a refrigerated cooler so as to maintain the reaction temperature below 30° C. After the bromine addition is complete, the reaction mass containing the suspended product is heated to 80° C. in order to dissolve essentially all of the 4,4'-isopropylidene-bis(2,6-dibromophenol) product. The organic phase is then contacted at 80° C. with 1 molar aqueous sodium sulphite solution—250 mL per mole 4,4'-isopropylidene-bis(2,6-dibromophenol)—and washed twice with deionized water. After each wash process, the aqueous phase is decanted off. In order to crystalize the product the organic phase is slowly cooled to 20° C. The solid suspension thus formed is then separated in a centrifuge and dried.

Examples 2 and 3 illustrate the heat treating step. TBBPA product made by another process and having ionic impurities was heat treated after rinsing the product with plant process water plant process water typically contains 150–200 ppm total dissolved solids.

EXAMPLE 2

A sample of TBBPA product (100 grams) having 66 ppm total ionics was filtered and washed with about 200 mL of plant process water. After washing the product, the product was heat treated at 140° C. for 2.5 days. Total ionics after the heat treating step was 30 ppm.

EXAMPLE 3

A sample of TBBPA (100 grams) was filtered and washed with about 200 mL of plant process water. Analysis of the washed wet cake indicated that the TBBPA product had a total ionic content of 40 ppm. The product was then heat treated at 140° C. for 16 hours. Total ionics after heat treating was 27 ppm.

In the next Examples (4 and 5), the TBBPA product made by another process was rinsed with deionized water prior to heat treating. The deionized water had a resistivity of about 100,000 ohms.

EXAMPLE 4

A sample of TBBPA product (100 grams) having 66 ppm total ionics was filtered and washed with 200 mL of deionized water having a resistivity of about 100,000 ohms. After washing the product, the product was heat treated at 140° C. for 2.5 days. Total ionics after the heat treating step was less than 2 ppm.

EXAMPLE 5

A sample of TBBPA product (100 grams) having 62 ppm total ionics was filtered and washed with about 200 mL of deionized water having a resistivity of about 100,000 ohms. After washing the product, the total ionics was 46 ppm. The sample was separated into three portions and heat treated at different temperatures. Analysis of the product rinsed with deionized water and subsequently heat treated are given in Table IV.

TABLE IV

| Sample | Temperature (°C.) | Time (Hrs) | Total Ionics (ppm) |
|---|---|---|---|
| 1 | 120 | 4 | <8 |
| 2 | 60–65 | 5 | 49 |
| 3 | 70 | 22 | 40 |
| 4 | 120 | 22 | 0 |

The process of this invention is applicable to flame retardant products comprised predominantly of brominated compounds derived from compounds represented by the following:

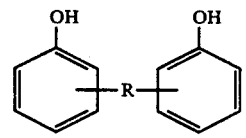

wherein R is a divalent aliphatic hydrocarbon group of 1–4 carbon atoms or a direct bond between two benzene rings. Representative examples are 4,4'-methylenebisphenol; 2,2'-methylenebisphenol; 2,4'-methylenebisphenol; 4,4'-ethylidenebisphenol; 2,2'-ethylidenebisphenol; 2,4'-ethylidenebisphenol; 2,2'-isopropylidenebisphenol; 2,4'-isopropylidenebisphenol; 4,4'-butylidenebisphenol; 2,2'-butylidenebisphenol; 4,4'-bisphenol; 2,2'-bisphenol; 2,4'-bisphenol and the like. These bisphenols can be substituted for the bisphenol-A, i.e., 4,4'-isopropylidenebisphenol, used in the fforegoing description and examples of the present invention. All of the brominated products can be used as fire retardants in a broad range of organic materials normally susceptible to combus-tion in the presence of air and an ignition source.

Other variations are possible within the spirit and scope of the appended claims.

What is claimed is:

1. A process for preparing a tetrabromobisphenol-A predominant product in high yield and high purity, comprising:
    a) forming a reaction solvent from at least one non-polar solvent and an amount of aqueous hydrogen peroxide;
    b) charging an amount of alkylidenediphenol to the reaction solvent to form a reaction mass;
    c) feeding an amount of bromine to the reaction mass at a temperature and for a period of time sufficient to tetrabrominate substantially all of the alkylidenediphenol thus
    d) maintaining during step (c) the amount of hydrogen peroxide less than an amount required to convert substantially all of the HBr which forms, to elemental bromine; and
    e) heat treating the formed product whereby a product having less than about 20 ppm ionic impurities is produced.

2. The process of claim 1 wherein the non-polar solvent is chlorobenzene.

3. The process of claim 1 wherein the heat treating is performed at a temperature above about 120° C.

4. The process of claim 1 wherein the amount of hydrogen peroxide is from about 0.9 to about 0.95 moles of hydrogen peroxide per mole of bromine.

5. The process of claim 1 wherein the amount of bromine ranges from about 2.05 to about 4.0 moles of bromine per mole of alkylidenediphenol.

6. The process of claim 1 wherein the aqueous hydrogen peroxide contains about 3 weight percent sulfuric acid.

7. The process of claim 1 wherein the reaction temperature is in the range of from about 0° to about 25° C.

8. The process of claim 1 further comprising washing the product with deionized water prior to heat treating.

9. The process of claim 1 wherein the alkylidenediphenol is 4,4'-isopropylidenediphenol.

10. The process of claim 4 wherein the heat treating is performed at a temperature above about 120° C. for a period of 30 seconds to an hour and wherein the amount of bromine ranges from about 2.05 to about 4.0 moles of bromine per mole of alkylidenediphenol.

11. An improvement in a process for preparing a 4,4'-isopropylidene-bis(2,6-dibromophenol) predominant product wherein 4,4'-isopropylidenediphenol is brominated in a chlorobenzene solvent, the improvement comprising
    a) providing an amount of aqueous hydrogen peroxide less than an amount required to oxidize substantially all of the HBr which forms during the bromination to bromine;
    b) separating the 4,4'-isopropylidene-bis(2,6-dibromophenol) product from the reaction mass;
    c) contacting the separated product with an amount of deionized water; and
    d) heat treating the product at a temperature and for a period of time whereby a product having less than about 20 ppm ionic impurities is formed.

12. The improvement of claim 11 wherein the heat treating is performed at a temperature above about 120° C.

13. The improvement of claim 11 wherein the heat treating is performed for a period of time of from about 30 seconds to about 1 hour.

14. The improvement of claim 11 wherein the amount of hydrogen peroxide is from about 0.05 to less than about 1.0 moles of hydrogen peroxide per mole of bromine.

15. The improvement of claim 14 wherein the amount of bromine ranges from about 2.05 to about 4.0 moles of bromine per mole of 4,4'-isopropylidenediphenol.

16. The improvement of claim 15 wherein the bromination is conducted at a temperature in the range of from about 0° to about 25° C.

17. The improvement of claim 16 wherein the weight percent 4,4'-isopropylidenediphenol to chlorobenzene solvent is in the range of from about 22 to about 29 weight percent.

18. The improvement of claim 17 wherein the heat treating is performed at a temperature above about 120° C. for a period of time of from about 30 seconds to about 1 hour.

19. A process for the co-production of a 4,4'-isopropylidene-bis(2,6-dibromophenol) predominant product and HBr, comprising:
    a) charging a reaction vessel with 4,4'-isopropyldienediphenol, and chlorobenzene solvent;
    b) brominating the 4,4'-isopropylidenediphenol with an amount of bromine sufficient to tetra-brominate substantially all of the 4,4'-isopropylidenediphenol, wherein the bromination is conducted in the substantial absence of hydrogen peroxide;
    c) separating the 4,4'-isopropylidene-bis(2,6-dibromophenol) and HBr products from the reaction mass;
    d) contacting the 4,4'-isopropylidene-bis(2,6-dibromophenol) product with an amount of deionized water; and
    e) heat treating the 4,4'-isopropylidene-bis(2,6-dibromo-phenol) product at a temperature above about 120° C. and for about 30 seconds to about 1 hour whereby a 4,4'-isopropylidene-bis(2,6-dibromo-phenol) predominant product having less than about 20 ppm ionic impurities is formed.

20. The improvement of claim 19 wherein the bromination is conducted at a temperature in the range of from about 0° to about 25° C.

21. The improvement of claim 20 wherein the amount of bromine ranges from about 4.0 to about 4.5 moles of bromine per mole of 4,4'-isopropylidenediphenol.

22. The improvement of claim 21 wherein the weight percent 4,4'-isopropylidenediphenol to chlorobenzene solvent is in the range of from about 22 to about 29 weight percent.

* * * * *

UNITED STATES PATENT AND TRADEMARK OFFICE
CERTIFICATE OF CORRECTION

PATENT NO. : 5,237,112
DATED : August 17, 1993
INVENTOR(S) : David E. LaRose

It is certified that error appears in the above-indentified patent and that said Letters Patent is hereby corrected as shown below:

Column 7, Line 27, reads "kylidenediphenol thus" and should read -- kylidenediphenol thus charged; --.

Signed and Sealed this

Twenty-sixth Day of July, 1994

Attest:

BRUCE LEHMAN

*Attesting Officer*     *Commissioner of Patents and Trademarks*